United States Patent [19]

Feucht

[11] Patent Number: 4,862,889
[45] Date of Patent: Sep. 5, 1989

[54] MONITORING CIRCUIT FOR AN RF SURGICAL APPARATUS

[75] Inventor: Peter Feucht, Berlin, Fed. Rep. of Germany

[73] Assignee: Siemens Aktiengesellschaft, Berlin and Munich, Fed. Rep. of Germany

[21] Appl. No.: 300,682

[22] Filed: Jan. 19, 1989

Related U.S. Application Data

[63] Continuation of Ser. No. 48,892, May 12, 1987, abandoned.

[30] Foreign Application Priority Data

Apr. 10, 1987 [DE] Fed. Rep. of Germany ....... 3711702

[51] Int. Cl.$^4$ .............................................. A61B 17/39
[52] U.S. Cl. ................................. 128/303.13; 128/908
[58] Field of Search ................... 128/303.13, 303.14, 128/303.15, 303.17, 303.18, 419 D, 908

[56] References Cited

U.S. PATENT DOCUMENTS

| | | | |
|---|---|---|---|
| 3,747,605 | 7/1973 | Cook | 128/419 D |
| 3,862,636 | 1/1975 | Bell et al. | 128/419 D |
| 4,122,854 | 10/1978 | Blackett | 128/303.13 |
| 4,126,137 | 11/1978 | Archibald | 128/303.14 |
| 4,687,004 | 8/1987 | Zenkich | 128/908 X |
| 4,712,544 | 12/1987 | Ensslin | 128/303.14 |

FOREIGN PATENT DOCUMENTS

| | | | |
|---|---|---|---|
| 3623688 | 1/1987 | Fed. Rep. of Germany | 128/303.14 |
| 58-94845 | 6/1983 | Japan | 128/303.13 |

Primary Examiner—Lee S. Cohen
Attorney, Agent, or Firm—Hill, Van Santen, Steadman & Simpson

[57] ABSTRACT

An RF surgical apparatus has an RF power stage, a control circuit for driving the power stage, and an adjustable element for setting a rated value of the output power. To monitor the RF surgical apparatus for the occurrence of an apparatus-caused malfunction, a power measuring unit measures the actual value of the RF power at the output of the RF power stage. Deviations of the actual value from a rated value are monitored. An alarm is generated if the deviation exceeds a selected value. An alarm can be simulated in a test mode by means of an auxiliary circuit.

14 Claims, 1 Drawing Sheet

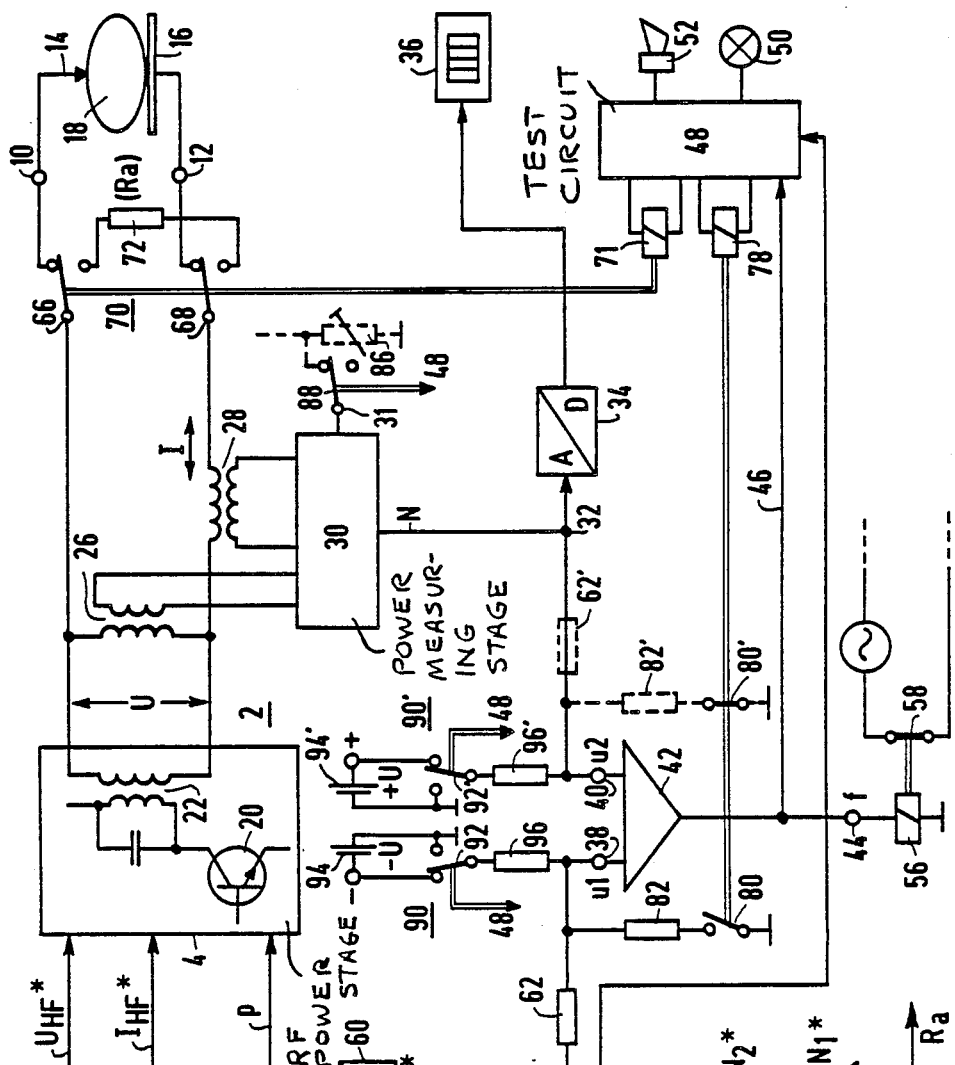
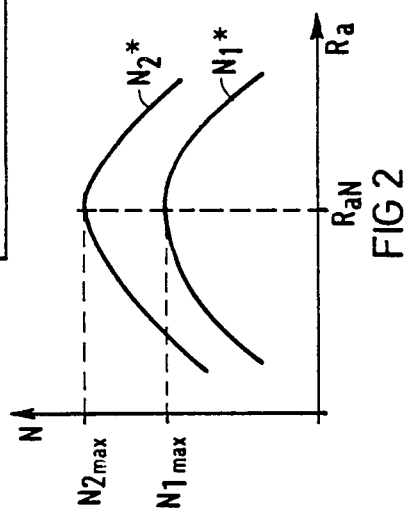
FIG 1
FIG 2

////

MONITORING CIRCUIT FOR AN RF SURGICAL APPARATUS

This is a continuation of application Ser. No. 048,892, filed May 12, 1987, now abandoned.

BACKGROUND OF THE INVENTION

1. Field of the Invention

The present invention is directed to a monitoring circuit for an RF surgical apparatus, and in particular, to a monitoring circuit for an RF surgical apparatus having an RF power stage and a control circuit for driving the power stage.

2. Description of the Prior Art

Various types of monitoring circuits are known in the field of RF surgery, such as the "Radiotom 804" manufactured by Siemens AG. The goal of most of these monitoring circuits is to protect the patient against undesired burns when cutting and/or coagulating. Regulations in many countries, such as "Medizingeraeteferordnung" (Deutsches Bundesgesetzblatt, Volume 1985, Part I, pages 93–98, Section 3) in West Germany, require that protective measures must be undertaken in medical devices so that patients, workers or third parties are not exposed to life and health hazards given proper employment of the apparatus, commensurate with the nature of the apparatus. It is also required that surgical devices, such as RF surgery devices, be equipped with a warning means to indicate an apparatus-caused incorrect dosage. Similar requirements are found in IEC 601, Part I, Section 51.

A so-called "first malfunction" is of particular interest in an RF surgical apparatus. The term "first malfunction" means a first apparatus-caused error. Given the occurrence of a first malfunction, the set power (for example, 100 watts) which can be lower than the maximum available output power (for example, 400 watts) should not be exceeded, or should be exceeded only by a defined tolerance value (for example, 30%). For this example, the output power should not exceed 130 watts given the occurrence of such an error, for example, in the power generating means or in the control means as a consequence of the outage of a component, such as a transistor.

SUMMARY OF THE INVENTION

It is an object of the present invention to provide a monitoring circuit for an RF surgical apparatus which has the capability of recognizing a so-called first malfunction.

The above object is achieved in accordance with the principals of the present invention in a monitoring circuit having an adjustment element for setting a rated value of the output RF power, a power measuring means for measuring the actual value of the output power connected at the output of the RF power stage, a load resistor having a predetermined resistance value connected to the output of the RF power stage, and a means for checking whether the actual value significantly deviates from the rated value. If such a deviation is detected, an output signal is generated for enabling an alarm, or for shutting the RF surgical device off.

It would be theoretically possible to devise an RF surgical apparatus having an RF power stage with an adjustment element for setting the output power thereof. An indicator measuring the power which is actually supplied as an output signal during work with the RF surgical apparatus could be utilized, as could a comparator for constantly comparing the output RF power to the set RF power and triggering an alarm when the set power is exceeded, or automatically disconnecting the surgical apparatus under such conditions. Such a power monitoring circuit, however, has the disadvantage that when switched on, the patient is included in the monitoring circuit via the neutral and active electrode, and could therefore be endangered given the occurrence of a malfunction. This disadvantage is avoided in the monitoring circuit disclosed herein by the use of the load resistor in the output circuit of the RF power stage.

DESCRIPTION OF THE DRAWINGS

FIG. 1 is a schematic block circuit diagram of an RF surgical apparatus including a monitoring circuit for the output power of the apparatus constructed in accordance with the principals of the present invention; and FIG. 2 is a resistance/power diagram for explaining the operation of the circuit shown in FIG. 1.

DESCRIPTION OF THE PREFERRED EMBODIMENTS

An RF surgical apparatus is generally referenced at 2 in FIG. 1. The apparatus 2 includes an RF power stage 4 and a control circuit 6 for driving the power stage 4. The control circuit switch has an adjustment element 8 for setting a rated value N* for the output RF power. The RF surgical apparatus 2 also includes two output terminals 10 and 12 to which an active electrode 14 and a neutral electrode 16 are respectively connected for performing cutting and/or coagulating operations on a patient 18. The maximum power $N_{max}$ which can be obtained from the output power stage 4 is defined by certain parameters. These include the operating voltage, the current, the drive of the output stage, the efficiency of the output stage, and the pulse shape of the output signal. For the discussion herein, it will be assumed that some of these parameters can be influenced by the adjustment element 8, and thus the prescribed RF power N* can be set. For example, the control circuit 6 may be a digital control circuit which prescribed digital values for the rated value of the RF voltage $U_{HF^*}$, the RF current $I_{HF^*}$ and which prescribes a pulse sequence p for driving circuit elements 20 within the RF power stage 4. In accord with the digital values $U_{HF^*}$, $I_{HF^*}$ and p selected in this manner, the power and output transformer 22 supplies a signal having power N to the output terminals 10 and 12, the power N corresponding to the rated value N* when no malfunction is present.

In the embodiments shown in FIG. 1, the power stage 4 generates an RF surgery signal for cutting and/or coagulating through a plurality of transistors, of which only one transistor 20 is shown, and via the power transformer 22. The RF surgery signal is taken without a connection to ground via the output terminals 10 and 12.

A fraction of the RF voltage U across the output lines of the RF power stage 4 is acquired without a voltage drop by a first transformer 26. An equivalent of the RF current I in one output line is measured analogously using a second transformer 28. The results of the voltage measurement from the transformer 26 and the current measurement from the transformer 28 are supplied to a watt-meter circuit, or to a power measuring unit 30, which identifies the effective power actually generated.

The power measuring stage 30 is preferably a multiplier, and operates by making a phase-accurate multiplication. Such multiplication elements are commercially available as integrated circuits, and the multiplication result has an error of less than 10%.

The result of the power measurement is the actual value N of the output RF power, or a proportion thereof. The actual value N is supplied through a connection 32 to an analog-to-digital converter 34, from which the value is supplied for numerical display on a display means 36. The current actual value N of the effective power output from the terminals 10 and 12 can be thus read by the operator.

Proceeding from the connection point 32, the value N is also supplied to an input 40 of a comparator 42. The input signal corresponding to the actual value N is referenced u2. The input signal u2 is compared in the comparator 42 to another input signal u1, which is supplied to an input 38. The input signal u1 is the rated value N*, or a signal proportional thereto. If the input signal u2 exceeds the input signal u1, i.e., the output power N exceeds the rated value N* (or exceeds the rated value with a certain tolerance), an enable signal f is supplied at the output 44 of the comparator 42. The physician or operator can be warned by an alarm by means of the enable signal f. This is symbolized by a connecting line 46 to a test circuit 48, having alarm elements such as an optical signalling means 50 and an acoustic signalling means 52. The enable signal f may alternatively be used to shut off the RF surgical apparatus 2. To that end, the output 44 is connected to a relay 56 which actuates a switch 58 which turns the voltage supply for the RF surgical apparatus 2 on and off.

The rated value N* set by the adjustment element 8 is taken from the control unit 6 as a digital value and is converted into the analog rated value N* in a digital-to-analog converter 60. The output of the converter 60 is supplied through a resistor 62 to the input 38 of the comparator 42. The analog rated value N* is constantly displayed on a display means 64.

During normal operation, in contrast to the test mode described below, the operator can see, by looking at the display units 36 and 64, if the actual and rated values N and N* of the RF power coincide. The monitoring circuit disclosed herein can also be operated in a test mode. After the actual value N of the RF power is acquired by the transformers 26 and 28, the RF surgery signal is supplied to the contacts 66 and 68 of a switching stage generally referenced at 70. The switching stage 70 preferably includes the contacts of a relay 71 which is driven by the test circuit 48. This drive is illustrated by double lines.

Normally, the RF surgery signal from the RF power stage 4 to the terminals 10 and 12 is also conducted to the electrodes 14 and 16 of the apparatus through further circuits as are known in the prior art and which are not shown in the drawing.

A load resistor 72, having a predetermined resistance value $R_a$ can be connected to the output of the power stage 4 by the switching stage 70, in place of the electrodes 14 and 16. After switching, the components 26, 28, 30, 42 and 60 as described above can be employed to check whether the actual value N significantly deviates from the rated value N*. By using the relay 71, the test circuit 48 can undertake an RF power test (self-test) at defined points in time. Such a self-test is initiated by actuating a test switch 74 connected in a line 76 between the control circuit 6 and the test circuit 48. When the switch 74 is closed, the test circuit 48 causes the desired switching of the relay 71. After switching, the contact 66 is connected to one side of the load resistor 72, and the contact 68 is connected to the other side of the load resistor 72. The load resistor 72 is thus connected to the power stage instead of the electrodes 14 and 16, and thus instead of the patient 18.

The output RF power, which is preferably the maximum power $N_{max}$ (as shown in FIG. 2), is measured with the assistance of the load resistor 72 during the self-test.

As shown in FIG. 2, the resistance value $R_a$ of the load resistor 72 is selected at $R_{aN}$, i.e., at a value such that the power stage 4 generates a maximum output value $N_{max}$ of the power N when the rated value N* is set. The value of the resistance $R_{aN}$ thus corresponds to the nominal value at which the maximum power is taken (N*=$N_{max}$). In other words, at every rated value N* that has been set (for example, $N_{1*}$=300 watts, or $N_{2*}$=350 watts), a single load resistor 72 (for example, having $R_{aN}$=500 ohms) results in maximum power emission ($N_{1max}$=$N_{1*}$=300 watts, or $N_{2max}$=$N_{2*}$=350 watts). The load resistor 72 is of approximately the same size for all rated values N* (for example, 300 watts or 350 watts).

When the RF surgical apparatus 2 is in proper working order, i.e., when there is no error or malfunction, the actual display 36 will correspond to the rated display 64 (with a certain tolerance). This check can be optically undertaken by an observer or operator, and can be made automatically by the comparator 42. Thus, a safety check and an overall monitoring of the RF surgical apparatus is possible. The value which is crucial for the safety of the patient 18, the output RF power, is thereby displayed. If a signficant (N* - N) occurs, this is an indication that a component malfunction exists. This automatically results in visual display at the display means 36 and 44, the generation of an alarm at the alarm elements 50 and 52, and/or to shut-down of the RF surgical apparatus by the switch 58.

FIG. 1 also includes circuitry for simulating an alarm. Such an alarm simulation is accomplished by shifting the threshold of the comparator 42. The input signal u1 at the input 38 of the comparator 42 is set at a predetermined value for the simulation. The test circuit 48, after actuation of the test switch 74, can also drive a second relay 78. This causes a switch 80 to be closed. The resistor 62 and a further resistor 82, in series with the switch 80 (one side of the switch 80 being connected to ground) results in an ohmic voltage divider for the analog voltage value N* at the comparator input 38. The two resistors 62 and 82 have values such that the tolerance limit for the actual value N, given a closed switch 80 and normal functioning, is just exceeded. The comparator 42 thus generates the enable signal f. In the present simulation case, this signal is only used for initiating an alarm. It will be understood that the relay 78 and the switch 80 preferably form one unit.

The two resistors 62 and 82 are specifically utilized for a negative tolerance. If a positive tolerance of the actual value N of the power is also possible during normal operation, a corresponding voltage divider, including resistors 62' and 82', which is disconnected by a corresponding switch 80', can be provided at the other input 40 of the comparator 42. These components are indicated in FIG. 1 in dashed lines. The elements 62, 78, 80 and 82, and 62', 78', 80' and 82' thus each represent an auxiliary circuit with which an alarm can be simulated in a test mode.

Instead of the relay-switch combination 78 and 80 or 78' and 80', an electronic switching means, for example, a switching transistor, may be used.

As stated above, the rated value N* may be reduced by a defined ratio using the ohmic voltage divider consisting of resistors 62 and 82 given actuation of the switch 80. A second possibility is to increase the actual value N by a defined ratio by eliminating the otherwise normally present voltage divider 62' and 82' by opening the switch 80'. Both auxiliary circuits are allocated to the comparator 42. Such an allocation is not absolutely necessary. A third possibility, therefore, is to increase the actual value N by a defined ratio by increasing the gain of the power measuring unit 30, or some other component. This is symbolized in FIG. 1 by a resistor 86 shown in dashed lines connected at a gain setting terminal 31 of the measuring stage 30, which can be connected or disconnected by a switch 88.

Lastly, an alarm may also be simulated by reducing the rated value N* by a defined absolute amount U, or by increasing the actual value N by a defined amount U. This may be achieved, for example, by shifting the comparator threshold by a corresponding amount U. This is indicated in FIG. 1 by a means 90 for switching the comparator threshold. The comparator threshold switching means 90 includes a switch 92, controlled by the test circuit 48, which applies either a negative voltage —U from a DC voltage source 94, or a reference potential, to the input 38 of the comparator 42 through a resistor 96. Alternatively, a switch 92' may supply either a positive voltage +U from a DC voltage source 94', or a reference potential, to the input 40 of the comparator 42 through a resistor 96'. The threshold switching means 90 and 90' are indicated with dashed lines.

The following is a summary of an operation using the first auxiliary circuit, with the other auxiliary circuits providing analogous operation. In the first test case, the "self-test," the relay 71 is actuated. The actual value display 36 and rated value display 64 must coincide within the scope of a defined tolerance, and the comparator 42 does not generate an alarm. In this case, the RF surgical apparatus 2 is free of a first malfunction. Such a check is undertaken not including the patient 18.

In the second case, the "alarm simulation," both relays 71 and 78 are actuated. In this case, the comparator 42 must trigger an alarm. A check can be undertaken to determine whether the monitoring means is functioning properly.

The overall test procedure can be automated such that the first and second tests (i.e., "self-test" and "alarm simulation") are successively executed by actuation by the test key 74, and are automatically interpreted. The apparatus 2 is error-free if the comparator 42 does not respond in the first test case, but does respond in the second test case. An apparatus malfunction must be present if the comparator 42 responds in the first test case or does not respond in the second test case. Under such circumstances, an alarm signal is generated and/or the apparatus 2 is inhibited. Executing such tests automatically also has the advantage that the load resistor 72 is only briefly loaded.

Although modifications and changes may be suggested by those skilled in the art, it is the intention of the invention to embody within the patent warranted hereon all changes and modifications as reasonably and properly come within the scope of his contribution to the art.

I claim:

1. A monitoring circuit for an RF surgical apparatus, said RF surgical apparatus having an RF power stage which generates an RF power output normally supplied to a patient via electrodes connected to an output of said RF power stage, and a control circuit for driving said RF power stage, said monitoring circuit comprising:
   adjustment means for connection to said control circuit for setting a rated value of the RF power output of said RF power stage;
   means for connection to the output of said RF power stage for continuously measuring the actual value of RF power output of said RF power stage by directly measuring the current and voltage at said output of said RF power stage;
   a load resistor having a predetermined resistance value;
   switching means for connecting said load resistor to the output of said RF power stage in place of said electrodes during a self-test of said monitoring circuit;
   a comparator having inputs respectively connected to said adjustment means and said means for measuring to which said rated value and said actual value are respectively continuously supplied, said comparator continuously determining deviation of said actual value from said rated value during supply of RF power to said patient and when said load resistor is connected to the output of said RF power stage during said self-test, said comparator having a threshold and generating an enable signal when said deviation exceeds said threshold; means for simultaneously actuating said switching means and supplying said rated value and said actual value to said inputs of said comparator to conduct said self-test;
   means for generating an alarm in response to said enable signal; and auxiliary circuit means connectable to said means for actuating for simulating a deviation in said comparator which exceeds said threshold.

2. A monitoring circuit as claimed in claim 1, wherein said predetermined resistance value of said load resistor is the nominal value at which said RF power stage an RF power output equal to said rated value.

3. A monitoring circuit as claimed in claim 1, wherein said adjustment means is a means for setting one of a plurality of rated values of the RF power output, and wherein said predetermined resistance value of said load resistor is the same for each of said plurality of rated values.

4. A monitoring circuit as claimed in claim 1, wherein said means for measuring the actual value of RF power output of said RF power stage has an adjustable gain, an wherein said auxiliary circuit means, comprises means for adjusting said gain of said means for measuring such that said deviation exceeds said threshold.

5. A monitoring circuit as claimed in claim 1, wherein said comparator has a first input to which said rated value is supplied and a second input to which said actual value is supplied, and wherein said auxiliary circuit means includes means for relatively adjusting the values supplied respectively to said first and second inputs such that the value at said first input is less than the value of said second input.

6. A monitoring circuit as claimed in claim 5, wherein said means for relatively adjusting includes means for reducing the value of said first input.

7. A monitoring circuit as claimed in claim 5, wherein said means for relatively adjusting includes means for increasing the value of said second input.

8. A monitoring circuit as claimed in claim 1, further comprising further switching means for selectively connecting said auxiliary circuit means to said comparator.

9. A monitoring circuit as claimed in claim 1, wherein said auxiliary circuit means includes at least one ohmic voltage divider.

10. A monitoring circuit as claimed in claim 1, further comprising means for simultaneously actuating said auxiliary circuit means and said comparator.

11. A monitoring circuit as claims in claim 10, wherein said means for simultaneously actuating said auxiliary circuit means and said comparator is a relay.

12. A monitoring circuit as claimed in claim 1, further comprising display means for displaying at least one of said actual value or said rated value.

13. A monitoring circuit as claimed in claim 1, wherein said means for generating an alarm is a means for generating an acoustic alarm.

14. A monitoring circuit as claimed in claim 13, wherein said means for generating an alarm is a means for generating an optical alarm.

* * * * *